United States Patent [19]

Denning et al.

[11] 4,225,576

[45] Sep. 30, 1980

[54] COMBINED RADIOIMMUNOASSAY FOR TRIIODOTHYRONINE AND THYROXINE

[75] Inventors: Charles E. Denning; Lloyd A. Schick, both of Elkhart, Ind.

[73] Assignee: Miles Laboratories, Inc., Elkhart, Ind.

[21] Appl. No.: 962,398

[22] Filed: Nov. 20, 1978

[51] Int. Cl.² .................................................. G01N 33/16
[52] U.S. Cl. ........................................ 424/1; 23/230 B; 23/230.6; 424/12
[58] Field of Search ............... 23/230 B, 230.6; 424/1, 424/12

[56] References Cited

U.S. PATENT DOCUMENTS

| | | | |
|---|---|---|---|
| 3,659,104 | 4/1972 | Gross et al. | 424/1 |
| 3,911,096 | 10/1975 | Chopra | 23/230 B |
| 3,928,553 | 12/1975 | Holland | 424/1 |
| 3,952,091 | 4/1976 | Grunberg et al. | 23/230 B |
| 3,961,894 | 6/1976 | Gordon et al. | 23/230.6 |

OTHER PUBLICATIONS

L. J. Unggren et al., Acta. Endocrinol., 81:487–494 (1976).
Haberman et al. J. Clin. Chem. Clin. Biochem., 14:495–601 (1976).

*Primary Examiner*—Benjamin R. Padgett
*Assistant Examiner*—Christine M. Nucker
*Attorney, Agent, or Firm*—Andrew L. Klawitter

[57] ABSTRACT

A method for the combined radioimmunoassay for the hormones triiodothyronine (T-3) and thyroxine (T-4) in serum or plasma, wherein the radiolabeled T-3 and T-4 reagents are T-3 and T-4 labeled with the same radioisotope. The hormones are extracted from the serum or plasma sample and separated from their binding proteins by adsopriton to a crosslinked dextran gel at a highly alkaline pH. After washing away the dissociated proteins, a predetermined limiting amount of T-3 antibody is incubated with the gel and thereafter radiolabeled T-3 which has become extracted from the gel by antibody binding is washed away. Excess T-3 antibody and a predetermined limiting amount of T-4 antibody are then incubated with the gel and radiolabeled T-3 and T-4 which has become extracted from the gel by antibody binding are thereafter washed away. The respective relative amounts of radiolabeled T-3 and T-4 retained by the gel after the incubations with the respective limiting amounts of T-3 and T-4 antibody are compared with standard results to quantitate the hormones in the sample. The use of excess T-3 antibody in the T-4 antibody incubation is critical to the accuracy of the method, enabling the use of the same radioisotope for radiolabeling T-3 and T-4.

9 Claims, 2 Drawing Figures

COMBINED RADIOIMMUNOASSAY FOR TRIIODOTHYRONINE AND THYROXINE

BACKGROUND OF THE INVENTION

1. Field of the Invention

This invention relates to radioimmunoassay methods for the quantitative determination of the iodothyronine hormones triiodothyronine (T-3) and thyroxine (T-4) in biological fluids such as serum. The present invention provides a unique method for the combined or concurrent radioimmunoassay of these hormones in serum or plasma wherein the same radioisotope is comprised in the radiolabeled T-3 and T-4 reagents used in the assay.

The secretion of T-3 and T-4 by the thyroid gland is controlled by thyrotropin (TSH), a thyroid-stimulating hormone from the anterior pituitary which in turn is controlled by a thyrotropin releasing hormone (TRH) secreted by the hypothalamus [Evered, *Clinics in Endocrinol. Metab.* 3, No. 3, W. B. Saunders and Co., Ltd. (1974)]. The first true assay for thyroid hormone was a competitive protein binding assay (CPBA) used by Ekins, *Clin. Chim. Acta* 5:453(1960), in which he used a radioactive tracer and thyroxine-binding globulin (TBG) as the primary hormone binder. The CPBA technique grew in popularity through the work of Murphy and Pattee [*J. Clin. Endocrinol. Metab.* 24:187–196(1964)] and others, and was the predominant testing method for T-4 until the advent of the radioimmunoassay (RIA).

Previously, T-4 was thought to be the primary hormone regulating metabolism. Little was known about the clinical significance of T-3 in the presence of the relatively large physiological levels of T-4. Gross and Pitt-Rivers [*Lancet* 1:439–441(1952)] were the first to identify T-3 as a thyroid hormone. With the advent of radioimmunoassay techniques [Brown et al, *Nature* 226:35(1970) and Neuman et al, *J. Clin. Invest.* 46:1346–1355(1967)], the measurement of serum T-3 has gained wide recognition as an important thyroid function test [Larson, *Metabolism* 21:1073–1092(1973); Hoffenburg, *Clin. Endocrinol.* 2:75–87(1973) and Harvard, *Brit. Med. J.* 1:553–556(1974)]. As much as 40% of circulating T-3 may be derived from the deiodination of circulating T-4 [Braverman et al, *J. Clin. Invest.* 49:855–864(1970)], and it has been estimated that as much as two-thirds of the normal thyroid hormonal effect can be attributed to T-3 [Sterling, *New Eng. J. Med.* 284:271–272(1971)].

The levels of T-3 and T-4 are normally maintained by their negative feedback effort in controlling the output of TSH. Generally, changes in T-3 levels are paralleled by similar changes in T-4, but in some circumstances the changes are independent. For example, a form of hyperthyroidism, T-3 toxicosis, has been described by Hollander [*Trans. Assoc. Am. Physicians* 81:76–91(1968)] and Sterling et al [*J. Am. Med. Assoc.* 213:571–575(1970)] in which the T-3 level is elevated while the T-4 level remains normal. Clearly, a single radioimmunoassay that would quantitate both total T-3 and T-4 in serum or plasma would be a convenient and valuable contribution to the comprehensive assessment of a patient's thyroid function status.

2. Brief Description of the Prior Art

Formerly, radioimmunoassay techniques were used primarily for the measurement of a single substance. More recently, since methods were developed to produce antisera having greater specificity, interest has grown in the application of RIA technology to concurrent measurement of more than one antigen. The present invention provides an RIA method for the combined measurement of T-3 and T-4 using the same radioisotope as tracer. A combined RIA method for these hormones must demonstrate considerable specificity since these two materials differ in structure by only a single iodine atom.

U.S. Pat. No. 3,659,104 discloses a method of measuring serum thyroxine employing an alkaline crosslinked dextran gel column to dissociate and separate the T-4 from serum protein. The method is unique in combining the extraction and saturation analysis steps on the same test device. This technique is applied to the determination of serum T-3 in U.S. Pat. No. 3,961,894. Neither of these patents suggests the combined determination of T-3 and T-4 nor any method capable of accomplishing such an assay.

A radioimmunoassay method for T-3 or T-4, or for T-3 and T-4, present in unextracted serum is described in U.S. Pat. No. 3,928,553. In the method, barbital or salicylate is used to inhibit thyroid hormone binding by serum prealbumin, and dilantin, salicylate, merthiolate, tetrachlorothyronine or 8-anilino-1-naphthalene sulfonic acid is used to inhibit the binding by thyroxine binding globulin. The method uses isotopically-labeled triiodothyronine ($^{125}$I T-3) and thyroxine labeled with a different radioisotope ($^{131}$I T-4). Separation of antibody-bound and unbound T-3 and T-4 is carried out by adsorption of the unbound portion on dextran coated charcoal, followed by centrifugation. No mention is made of the specificity of the assay for T-3 and for T-4 and therefore their independence in the assay is undescribed.

A very similar procedure for determining both T-3 and T-4 using T-3 and T-4 labeled with different radioisotopes ($^{125}$I and $^{131}$I, respectively) is described by Ljunggren et al, *Acta. Endocrinol.* 81:487–494(1976). Detectable levels of contaminant T-3 were found in the standard T-4 solution requiring a correction factor. Also, the influence of $^{131}$I on the counting of $^{125}$I was found to be in the area of 20 percent.

Habermann et al, *J. Clin. Chem. Clin. Biochem.* 14:595–601(1976), describe a combined RIA procedure for T-3 and T-4 in urine with no application to assaying serum or plasma. In urine, T-3 and T-4 are present in similar concentrations whereas T-3 appears in much lower concentrations than T-4 in serum. Also, protein binding of T-3 and T-4 is a significant factor to deal with in assays of serum but not so for urine assays. In the Habermann et al method, a sample of a 24-hour urine pool is applied to a dextran gel column equilibrated with a highly alkaline solution. Radiolabeled ($^{125}$I) T-3 and T-4 are added to the column which is then washed with buffer at pH 7.4. After incubating T-3 antibody on the column for 2 hours, the antibody bound T-3 is eluted with the buffer. Then T-4 antibody is incubated on the column for 2 hours and antibody bound T-4 eluted with buffer. The radioactive T-3 and T-4 eluates are then measured separately and compared to standard results. This method could not take advantage of measuring radioactivity on the columns because of the presence of radiometrically indistinguishable $^{125}$I T-3 and $^{125}$I T-4 on the column throughout the method.

U.S. Pat. No. 3,952,091 describes a simultaneous multiple radioimmunoassay providing a qualitative indication of the presence of one or more of a specific group of antigens. The assay is a simple screening test which cannot distinguish one antigen from another and cannot provide quantitative results.

SUMMARY OF THE INVENTION

It has now been found that a rapid, convenient and highly accurate combined T-3 and T-4 radioimmunoassay of a serum or plasma is provided by conducting the following steps:

(a) contacting a crosslinked dextran gel at a pH of at least 11 with the serum or plasma sample and with radiolabeled T-3 and T-4 labeled with the same radioisotope, (b) washing the gel with an alkaline aqueous solution having a pH less than 11, (c) incubating the gel with a predetermined first amount of an antibody to T-3 insufficient to bind all of the radiolabeled T-3 bound to the gel at the conclusion of step (b), (d) washing the gel with an alkaline aqueous solution having a pH less than 11, said gel retaining a portion of the radiolabeled T-3 bound thereto as a direct function of the amount of T-3 present in the sample, (e) incubating the gel with a predetermined second amount of an antibody to T-3 sufficient to bind all of the radiolabeled T-3 bound to the gel at the conclusion of step(d) and with a predetermined amount of an antibody to T-4 insufficient to bind all of the radiolabeled T-4 bound to the gel at the conclusion of step(d), (f) washing the gel with an alkaline aqueous solution having a pH less than 11, said gel retaining substantially no radiolabeled T-3 while retaining a portion of the radiolabeled T-4 bound thereto as a direct function of the amount of T-4 present in the sample, and (g) comparing (1) the relative amounts of radiolabeled T-3 and T-4 retained by the gel after wash steps(d) and (f), respectively, with respect to the amounts of radiolabeled T-3 and T-4 contacted with the gel in step(a), to (2) such relative amounts obtained by performing the same method on standard samples containing known amounts of T-3 and T-4.

In step(a), the highly alkaline environment dissociates T-3 and T-4 from their endogenous binding proteins, principally thyroxine binding globulin (TBG), and favors adsorption of the dissociated T-3 and T-4, along with the radiolabeled T-3 and T-4, to the crosslinked dextran gel. The wash solution in step(b) simultaneously removes the dissociated binding proteins and any potentially interfering free radioactive isotope while lowering the pH of the gel environment to below 11 whereat unlabeled and radiolabeled T-3 and T-4 remain adsorbed to the gel but are available for binding to antibody with consequent desorption from the gel.

During incubation step(c), the limiting amount of T-3 antibody serves as a competitive binder for unlabeled T-3 and radiolabeled T-3. This competition is unaffected by sample T-4 and radiolabeled T-4 due to the very low cross reactivity of T-3 antibody. The amount of radiolabeled T-3 which can successfully become bound to antibody, and consequently desorbed from the gel, is inversely related to the amount of T-3 present in the sample. This fraction of the radiolabeled T-3 is removed during wash step(d), leaving an amount of radiolabeled T-3 retained by the gel as a direct function of the amount of T-3 present in the sample.

A second amount of T-3 antibody is incubated with the gel in step(e) and is an excess quantity capable of binding and desorbing from the gel substantially all of the remaining unlabeled and radiolabeled T-3 to prevent any affect on the measurement of radiolabeled T-4 retained by the gel after incubation with the T-4 antibody. The fraction of radiolabeled T-4 which becomes bound to antibody, and consequently desorbed from the gel, and all of the remaining unlabeled and radiolabeled T-3 which becomes bound to the excess T-3 antibody are removed from the gel in wash step(f), leaving an amount of radiolabeled T-4 (and no radiolabeled T-3) retained by the gel as a direct function of the amount of T-4 present in the sample. It has been found that significant inaccuracies can arise if substantially all radiolabeled T-3 is not removed from the gel with the excess T-3 antibody. Any radiolabeled T-3 left on the column would otherwise be misinterpreted as additional radiolabeled T-4 because the same radioisotope is used for labeling both hormones.

While after wash step(f) only radiolabeled T-4 remains bound to the gel and is a function of the T-4 concentration in the sample, at the time that radiolabeled T-3 bound to the gel is related to sample T-3 concentration, i.e., after wash step(d), a significant amount of radiolabeled T-4, labeled with the same radioisotope as the radiolabeled T-3, is present and must be accounted for mathematically to determine the relative amount of radiolabeled T-3 only retained by the gel after the T-3 antibody competitive binding step. This step, step(g), is advantageously accomplished by measuring the radioactivity of the incubating gel in step(c) ("first count"), of the incubating gel in step(e) ("second count"), and of the washed gel from step(f) ("third count"); by calculating T-3 and T-4 retention ratios as follows:

$$\frac{T\text{-}3}{\text{retention}} = \frac{T\text{-}3 \text{ total count} - (\text{first count} - \text{second count})}{T\text{-}3 \text{ total count}}$$

$$\frac{T\text{-}4}{\text{retention}} = \frac{\text{third count}}{T\text{-}4 \text{ total count}}$$

(or multiples thereof such as percentages) wherein T-3 total count and T-4 total count are, respectively, the total radioactivity of the radiolabeled T-3 and T-4 contacted with the gel in step(a); and by comparing such ratios to those obtained by performing the same assay method on standard samples containing known amounts of T-3 and T-4. For the optimal assay, T-3 total count is determined experimentally by separately performing the method through step(c), contacting the gel in step(a) with the radiolabeled T-3 but not the radiolabeled T-4 or the sample, and measuring the radioactivity of the washed gel after step(b); and T-4 total count likewise is determined experimentally by separately performing the method through step(d), contacting the gel in step(a) with the radiolabeled T-4 but not the radiolabeled T-3 or the sample, and measuring the radioactivity of the washed gel at step(d).

Preferred crosslinked dextran gels are those crosslinked with an epihalohydrin as described in U.S. Pat. No. 3,042,667 and having a water regain of from about 1 to 5 grams per gram of dry gel. Such gels are produced commercially by Pharmacia AB, Uppsala, Sweden, and are sold under the trademark Sephadex ® in various ranges of molecular weight and seive size. Of these gels, the most preferred is that which is sold under the trademark Sephadex G-25 which comprises dextran gel crosslinked with epichlorohydrin and which has a water regain of about 2.5 grams per gram of dry gel.

The wash solutions used in steps(b), (d) and (f) are preferably buffer solutions having a pH of between 7 and 10. Various inorganic buffers, such as phosphate buffers, and various organic buffers, such as tris(hydroxymethyl)aminomethane, may be used. A particularly preferred buffer is a barbital buffer having a pH of about 8.6.

While the radiolabeled T-3 and T-4 may be labeled with any suitable radioisotope, such as $^{14}C$, it is preferred to label T-3 and T-4 by substituting for a normally nonradioactive iodine atom in their respective molecular structures, a radioactive iodine such as $^{131}I$, but preferably $^{125}I$ because of its longer half life.

The assay method is preferably accomplished by using a column packed with the dextran gel to faciitate the introduction of reagents and the samples, incubations, wash steps, and measurement of radioactivity of the gel. Further preferred embodiments and advantages of the present invention will be evident from the examples to follow.

Figure 1:
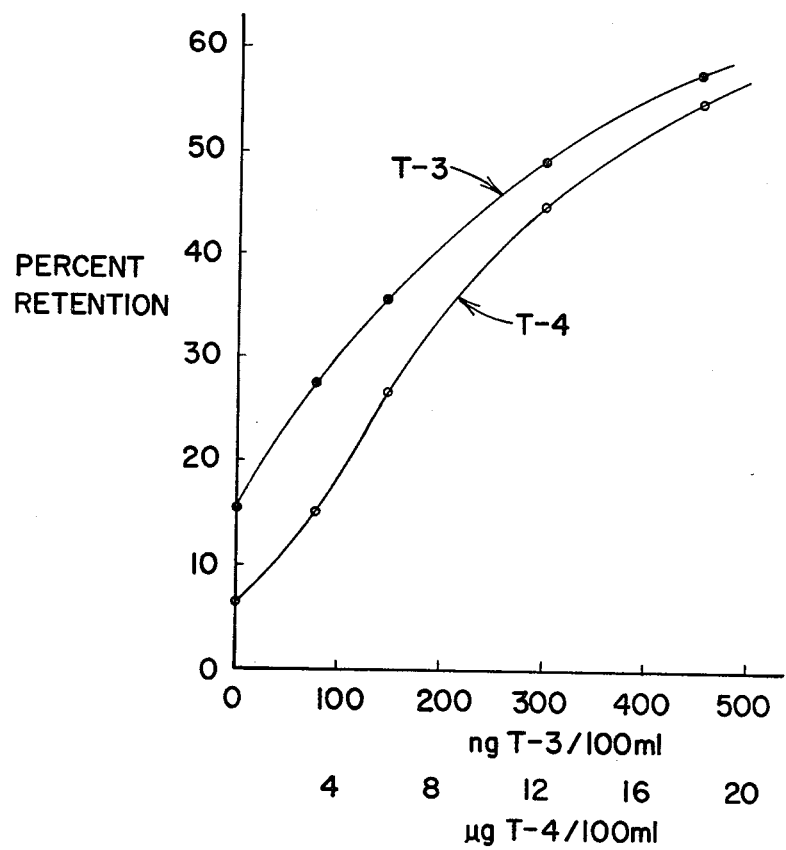
FIG. 1 is a graphical representation of typical T-3 and T-4 standard curves produced by performing the present method on samples containing known amounts of the hormones.

The invention will now be illustrated, but is not intended to be limited, by the following examples.

MATERIALS

Columns (1.2×1.6 cm) containing a fine crosslinked dextran gel (Sephadex ® G-25 brand, Pharmacia AB, Uppsala, Sweden) were obtained from TETRALUTE ® thyroid function test kits available from the Ames Company Division of Miles Laboratories, Inc., Elkhart, Ind. L-thyroxine sodium salt (B grade) was obtained from Calbiochem, Elk Grove Village, Ill., and L-3,3',5-triiodothyronine (free acid) from ICN Biochemicals, Cleveland, Ohio. TETRAMET ® $^{125}I$-thyroxine (3.81 mg T-4/liter, 244 mC$_i$/liter and 64 mC$_i$/mg) was obtained from Abbott Laboratories, North Chicago, Ill. $^{125}I$-triiodothyronine (26.36 μg T-3/liter, 58 mC$_i$/liter, and 2.2 C$_i$/mg) was obtained from Ames-Yissum Ltd., Jerusalem, Israel, having been prepared by a standard procedure [Weeke and Orskov, *Scand. J. Clin. Lab. Invest.* 32:357–360(1973)]. Triiodothyronine antiserum was obtained from Miles-Yeda, Rehovot, Israel and antiserum to thyroxine was prepared by immunization of rabbits with a T-4-bovine serum albumin conjugate according to the method of Mitsuma et al, *Biochem. Biophys. Res. Commun.* 46:2107–2113 (1972). Sixty clinical serum specimens were obtained from the Radioisotopes Department of the South Bend Medical Foundation (SBMF), South Bend, Ind. which also provided reference assay values for thyroxine using test kits from Nuclear Medical Systems, Newport Beach, Calif. Additionally, 12 pregnancy sera were provided by Elkhart General Hospital, Elkhart, Ind. and another 14 clinical sera were obtained from the University of Massachusetts Medical Center, Worchester, Mass. which also furnished reference values for triiodothyronine and thyroxine using SERALUTE ® Total T-3 and TETRALUTE ® Total T-4 test kits available from the Ames Company Division of Miles Laboratories, Inc. Thyroxine reference values for the pregnancy sera were determined using TETRALUTE kits and triiodothyronine reference values for these sera and the 60 sera from SBMF were established using SERALUTE Total T-3 (RIA) kits. Finally, triiodothyronine reference values were determined for all 86 clinical sera using the T-3 RIA kit of Amersham/Searle Corp., Arlington Heights, Ill. Norit A (neutral) charcoal was obtained from Schwarz/Mann, Orangeburg, N.Y. and normal human serum from Elkhart General Hospital. Sephadex G-25 (fine) was supplied by Pharmacia Fine Chemicals, Inc., Piscataway, N.J. The buffer used in the combined radioimmunoassay for T-3 and T-4 was prepared from 15.4 g sodium barbital and 2.76 g barbital dissolved in one liter of glass distilled water (approximately 75 mM, pH 8.6). All measurements of radioactivity were made with a GAMMACORD ® gamma-counting instrument from the Ames Company Division of Miles Laboratories, Inc.

METHODS

Preparation of Standard Mixtures of T-3 and T-4

A stock solution consisting of 36 milligrams (mg) of triiodothyronine (free acid) dissolved in 50 milliliters (ml) of a 1:1 volume:volume mixture of 0.1 N sodium hydroxide and ethylene glycol was prepared. This stock solution was diluted with 0.1 N sodium hydroxide to produce T-3 concentrations of 150, 300, 600 and 900 nanograms (ng)/100 ml. Also, a ten-fold dilution of the stock solution was made with 0.1 N sodium hydroxide to verify the T-3 concentration by measuring the absorbance at 315 nanometers (nm) versus 0.1 N sodium hydroxide as the blank, using 4585 $M^{-1}$ $cm^{-1}$ as the molar absorbance. An absorbance of 0.486 was obtained which is equivalent to $1.060 \times 10^{-4}$ moles T-3/liter.

T-4 was purified by chromatographic fractionation of 10 mg of B grade L-thyroxine (sodium salt) on a 1.5×30 centimeter (cm) column of Sephadex G-25 (fine) equilibrated with 0.01 N sodium hydroxide. The elution profile was monitored at 340 nm and the fractions corresponding to the thyroxine peak were pooled. The T-4 concentration of this thyroxine pool was determined by measuring the absorbance at 325 nm, using 6207 $M^{-1}$ $cm^{-1}$ as the molar absorbance. An absorbance of 0.368 was obtained which is equivalent to $5.929 \times 10^{-5}$ moles T-4/liter. The T-4 stock solution was diluted with 0.1 N sodium hydroxide to produce thyroxine concentrations of 6.0, 12.0, 24.0 and 36.0 micrograms (μg)/100 ml.

Working standards consisted of mixtures of triiodothyronine and thyroxine which were prepared from the T-3 and T-4 dilutions by making 1:1 volume:volume mixtures, thus:

| 1 Volume T-3 Solution + ng/100 ml | 1 Volume T-4 Solution → μg/100 ml | Standard Mixture | |
|---|---|---|---|
| | | T-3 ng/100 ml | T-4 μg/100 ml |
| 150 | 6.0 | 75 | 3.0 |
| 300 | 12.0 | 150 | 6.0 |
| 600 | 24.0 | 300 | 12.0 |
| 900 | 36.0 | 450 | 18.0 |

Preparation of $^{125}I$ T-3 and $^{125}I$ T-4 Mixture $^{125}I$-Monolabeled 3,3',5-triiodothyronine of high specific activity (2.2 C$_i$/mg) was shown to have a free iodide content less than 10%. This stock solution of $^{125}I$ T-3 (26.36 μg T-3/liter) was diluted 1 to 67.67 with 0.1

N sodium hydroxide. A stock solution of $^{125}$I T-3 (3.81 mg/liter) was separately diluted 1 to 835 with 0.1 N sodium hydroxide. Then, a working mixture of $^{125}$I T-3 and $^{125}$I T-4 was prepared by making a 1:1 volume:-volume mixture of the diluted radioactive hormones so that the final dilution factor for $^{125}$I T-3 and 135.3 and 1670 for $^{125}$I T-4. The resulting concentration of T-3 in the mixture was 195 ng/liter (0.30 nM) and the concentration of T-4 was 2.3 μg/liter (2.96 nM). Thus, an application of 200 μl of the $^{125}$I T-3 and $^{125}$I T-4 mixture on a Sephadex G-25 column was equivalent to an input of 39 picograms (pg) [0.06 picomole (pmole)] T-3 and 460 pg (0.59 pmole) T-4. Also, 200 μl of the mixture emitted about 50,000 counts per minute (cpm) each from $^{125}$I T-3 and $^{125}$I T-4, a total of about 100,000 cpm.

Preparation of $^{125}$I T-3 and $^{125}$I T-4 for Total Count Controls $^{125}$I T-3 and $^{125}$I T-4 for the total count controls are made by preparing individual isotope solutions at the same final dilution as for the $^{125}$I T-3-$^{125}$I T-4 mixture. These total-count controls are used for the separate and independent calculation of percent retention of T-3 and T-4.

Charcoal Extraction of T-3 and T-4 from Human Serum

Thyroid hormones were removed from serum by Norit A (neutral) charcoal extraction similar to the procedure of Mitsuma et al. *Biochem. Biophys. Res. Commun.* 46:2107–2113 (1972). Seventeen grams of charcoal and 325 ml serum were incubated for 21 hours with mixing at 4° C. The resulting slurry was centrifuged in a refrigerated centrifuge (4° C.) at 12,000 revolutions per minute (rpm) for 25 minutes and the supernatant layer was centrifuged for another 110 minutes at 14,200 rpm. Assays using the SERALUTE and TETRALUTE test kits for the determination of T-3 and T-4 in serum failed to detect any T-3 or T-4 in the final supernatant. A final filtration of the serum was made through a membrane of average pore size 0.2 μm.

Preparation and Dilution of Antisera Reagents

Triiodothyronine antiserum was diluted 1:1700 in barbital buffer. This dilution of T-3 antiserum was used for the first incubation phase (T-3 determination) of the radioimmunoassay method and results in the binding of about 85% of the tracer $^{125}$I T-3 in the absence of non-radioactive T-3.

The second incubation phase (T-4 determination) of the combined method is accomplished with a mixture of T-3 and T-4 antisera which was prepared as follows: barbital buffer was used to dilute T-3 antiserum 1:150 and T-4 antiserum 1:15. These two antisera solutions were mixed 1:1 volume:volume so that the final dilution of T-3 antiserum used in the mixture was 1:300 and the final dilution of T-4 antiserum was 1:30. This dilution of T-4 antiserum results in the binding of about 94% of $^{125}$I T-4 in the absence of nonradioactive T-4. The presence of T-3 antiserum in the mixture removes virtually all T-3 from the column during the second incubation phase of the method and thus eliminates any significant interference from $^{125}$I T-3 in the determination of $^{125}$I T-4.

Test Procedure for the Combined T-3 and T-4 Radioimmunoassay

All tests were performed in duplicate at room temperature. The top caps of the Sephadex G-25 columns from the TETRALUTE test kits were removed and the excess liquid above the Sephadex gel was discarded. To the top of columns to be used in testing samples was added, in the following order, 0.2 ml of the mixture of $^{125}$I T-3 and $^{125}$I T-4 (approximately 100,000 cpm) in 0.1 N sodium hydroxide, 0.2 ml of serum sample and 0.2 ml of 0.1 N sodium hydroxide. The columns to be used in testing standards received 0.2 ml of the isotope mixture, 0.2 ml of serum free of T-3 and T-4, and 0.2 ml of a standard mixture of T-3 and T-4 in 0.1 N sodium hydroxide. Total count-control columns received 0.2 ml of either $^{125}$I T-3 (50,000 cpm) or $^{125}$I T-4 (50,000 cpm), 0.2 ml of serum free of T-3 and T-4 and 0.2 ml 0.1 N sodium hydroxide. The concentration and cpm of $^{125}$I T-3 in the isotope mixture were identical to that added to the T-3 duplicate total count-control columns. Likewise, the T-4 concentration and cpm of $^{125}$I T-4 were the same in the isotope mixture and the duplicate T-4 total count-control columns. All of the columns (samples, standards, and total count-controls) were placed over a drain rack and the contents of the columns above the Sephadex gel bed were mixed by gentle swirling. The bottom caps were removed, allowing the columns to drain. The columns were then washed with 4 ml barbital buffer. Then to each column, except the duplicate $^{125}$I T-3 total-count control columns, was added 0.5 ml of the diluted T-3 antiserum. The $^{125}$I T-3 total count-control columns received 0.5 ml barbital buffer instead of T-3 antiserum. During an ensuing 40-minute incubation, a determination of the radioactivity ("first count") in each column was made. The first count (cpm) of the $^{125}$I T-3 total count-control columns was recorded as the "T-3 Total Count" and then the T-3 total count-control columns were discarded. At the conclusion of the incubation step, antibody-bound T-3 was eluted from the remaining columns by washing with 4 ml of barbital buffer. After the columns completely drained, 0.5 ml of the mixture of diluted T-4 and T-3 antisera was added to each column, except the $^{125}$I T-4 total count-control columns which received 0.5 ml of barbital buffer instead of the antisera mixture. A 20-minute incubation period followed during which the level of radioactivity in each column was determined ("second count"). The second count of the $^{125}$I T-4 total count-control columns was recorded as the "T-4 Total Count" and then the T-4 total count-control columns were discarded. The second count of the other columns was used in calculating the percent retention of T-3 on the columns after the elution of antibody-bound T-3. Upon completion of the second incubation step, antibody-bound T-4 was eluted from the remaining columns (samples and standards) by washing with 4 ml of barbital buffer. The final wash also eluted virtually all $^{125}$I T-3 from the columns. A third determination ("third count") of the level of radioactivity in each remaining column was made. This last count was used in calculating the percent retention of T-4 on the columns. Standard curves were constructed for T-3 and T-4 in which percent retention was plotted as a function of the thyroid hormone concentration where:

$$\text{T-3 Percent Retention} = \frac{\text{T-3 Total Count} - (\text{first count} - \text{second count})}{\text{T-3 Total Count}} \times 100$$

and $$\text{T-4 Percent Retention} = \frac{\text{third count}}{\text{T-4 Total Count}} \times 100$$

Typical T-3 and T-4 standard curves are shown in FIG. 1 of the drawings.

RESULTS

Precision and Sensitivity

The intra- and inter-assay reproducibility of the T-3 and T-4 standard curves was determined from 12 standard curves run on separate days. All standards were run in duplicate and the mean percent retention at each level of standard was plotted as a function of the standard concentration. The data given in Table 1 below show the mean retention values and the inter-assay standard deviation obtained from the separate standard curves. The intra-assay standard deviation given in Table 1 was calculated from the differences between duplicate determinations at each standard level. On the basis of concentration, the average intra- and inter-assay relative standard deviation for the T-3 standard curve was determined to be 11.5 and 17.0%, respectively, whereas the corresponding values for the T-4 standard curve are 5.9 and 9.5%.

The intra- and inter-assay reproducibility of the method was also determined from the measured T-3 and T-4 levels in sera in each of the three clinical ranges; hypothyroid, euthyroid, and hyperthyroid (Table 2). Sera within each clinical range were pooled and 20 determinations were made on the same day for each of the three serum pools and 12 determinations were made on separate days. The mean T-3 values determined within the same day for the three serum pools were 37, 97 and 314 ng/100 ml, respectively, for the low, intermediate and high level pools and the corresponding values for T-4 were 3.5, 6.9 and 16.8 µg/100 ml. The day-to-day mean T-3 values were determined to be 51, 119 and 322 ng/100 ml, respectively, for the low, intermediate and high level serum pools whereas the corresponding values for T-4 were 3.3, 6.8 and 17.1 µg/100 ml.

TABLE 1

Intra- and Inter-Assay Precision of Standard Curves

| | Inter-Assay | | | | | Intra-Assay | | | |
|---|---|---|---|---|---|---|---|---|---|
| Std. Conc. | Mean % Retention | S.D.[a] of the % Retention | Rel. Std.[b] Dev. (%) | S.D. | Rel. Std.[c] Dev. (%) | S.D.[d] of the % Retention | Rel. Std.[b] Dev. (%) | S.D. | Rel. Std.[c] Dev. (%) |
| ng T-3/100 ml | | | | ng/100 ml | | | | ng/100 ml | |
| 0 | 15.7 | 2.0 | 12.7 | — | — | 0.8 | 5.1 | — | — |
| 75 | 26.8 | 2.5 | 9.3 | 21 | 28.0 | 1.4 | 5.2 | 11 | 14.7 |
| 150 | 34.9 | 2.0 | 5.7 | 20 | 13.3 | 2.1 | 6.0 | 21 | 14.0 |
| 300 | 49.0 | 2.7 | 5.5 | 35 | 11.7 | 2.3 | 4.7 | 27 | 9.0 |
| 450 | 57.4 | 2.9 | 5.1 | 68 | 15.1 | 1.6 | 2.8 | 38 | 8.4 |
| µg T-4/100 ml | | | | µg/100 ml | | | | µg/100 ml | |
| 0 | 6.7 | 0.8 | 11.9 | — | — | 0.4 | 6.0 | — | — |
| 3 | 15.6 | 1.2 | 7.7 | 0.3 | 10.0 | 0.8 | 5.1 | 0.2 | 6.7 |
| 6 | 28.0 | 2.1 | 7.5 | 0.6 | 10.0 | 1.1 | 3.9 | 0.3 | 5.0 |
| 12 | 44.4 | 2.4 | 5.4 | 1.2 | 10.0 | 1.2 | 2.7 | 0.6 | 5.0 |
| 18 | 54.5 | 2.0 | 3.7 | 1.4 | 7.8 | 1.8 | 3.3 | 1.2 | 6.7 |

[a] Standard Deviation (S.D.) calculated from the means of duplicate determinations done on 12 sets of standard curves; $\text{S.D.} = \pm\sqrt{\frac{\Sigma(x-\bar{x})^2}{n-1}}$

[b] Rel. Std. Dev. = Relative Standard Deviation = $\frac{\text{S.D.}}{\bar{x}} \times 100$

[c] Rel. Std. Dev. = Relative Standard Deviation = $\frac{\text{S.D.}}{\text{Std. Conc.}} \times 100$

[d] $\text{S.D.} = \pm\sqrt{\frac{\Sigma d^2}{2n}}$

Where:
d = difference between duplicate pairs
n = number of duplicate pairs (12)

TABLE 2

Intra- and Inter-Assay Reproducibility of T-3 and T-4 Levels for Sera In Three Clinical Ranges

| | Clinical Range | n | Mean ng T-3/ 100 ml | S.D.[e] | Rel. Std. Dev. (%)[f] | Mean µg T-4/ 100 ml | S.D.[e] | Rel Std. Dev. (%) |
|---|---|---|---|---|---|---|---|---|
| | hypothyroid | 12 | 51 | 14 | 27.5 | 3.3 | 0.2 | 6.1 |
| Inter-Assay | euthyroid | 12 | 119 | 23 | 19.3 | 6.8 | 0.5 | 7.4 |
| | hyperthyroid | 12 | 322 | 36 | 11.2 | 17.1 | 1.3 | 7.6 |
| | hypothyroid | 20 | 37 | 10 | 27.0 | 3.5 | 0.2 | 5.7 |
| Intra-Assay | euthyroid | 20 | 97 | 14 | 14.4 | 6.9 | 0.4 | 5.8 |
| | hyperthyroid | 20 | 314 | 19 | 6.1 | 16.8 | 0.5 | 3.0 |

[e] $\text{S.D.} = \pm\sqrt{\frac{\Sigma(x-\bar{x})^2}{n-1}}$

[f] Rel. Std. Dev. = Relative Standard Deviation = $\frac{\text{S.D.}}{\bar{x}} \times 100$ The sensitivity of the assay is defined here as the detection limit, the smallest concentration of thyroid hormone which can be reliably differentiated from zero.

Two standard deviations of the retention at zero concentration corresponds to a T-3 concentration of approximately 26 ng/100 ml (52 pg/column) and a T-4 concentration of approximately 1.0 μg/100 ml (2 ng/column). These degrees of sensitivity are adequate for the measurement of triiodothyronine and thyroxine in clinical specimens.

Specificity

The specificity of the antisera for the combined radioimmunoassay of T-3 and T-4 was examined by determining the cross reactivity of T-3 antiserum with T-4, and the cross reactivity of T-4 antiserum with T-3. The degree of cross reactivity was defined as the concentration of thyroid hormone needed to give 50% inhibition divided by the concentration of cross-reactive test compound necessary to give the same inhibition times 100. The degree of cross reactivity of T-4 antiserum with T-3 was determined to be 8.7%. At this degree of cross reactivity, endogenous levels of T-3 would not significantly affect thyroxine determinations. The degree of cross reactivity of T-3 antiserum with T-4 was 0.20 and 0.025%, respectively, for B grade T-4 and B grade T-4 purified by Sephadex G-25 chromatography to remove T-3 -contamination. In all assays conducted here, only the purified T-4 was used.

Figure 2:
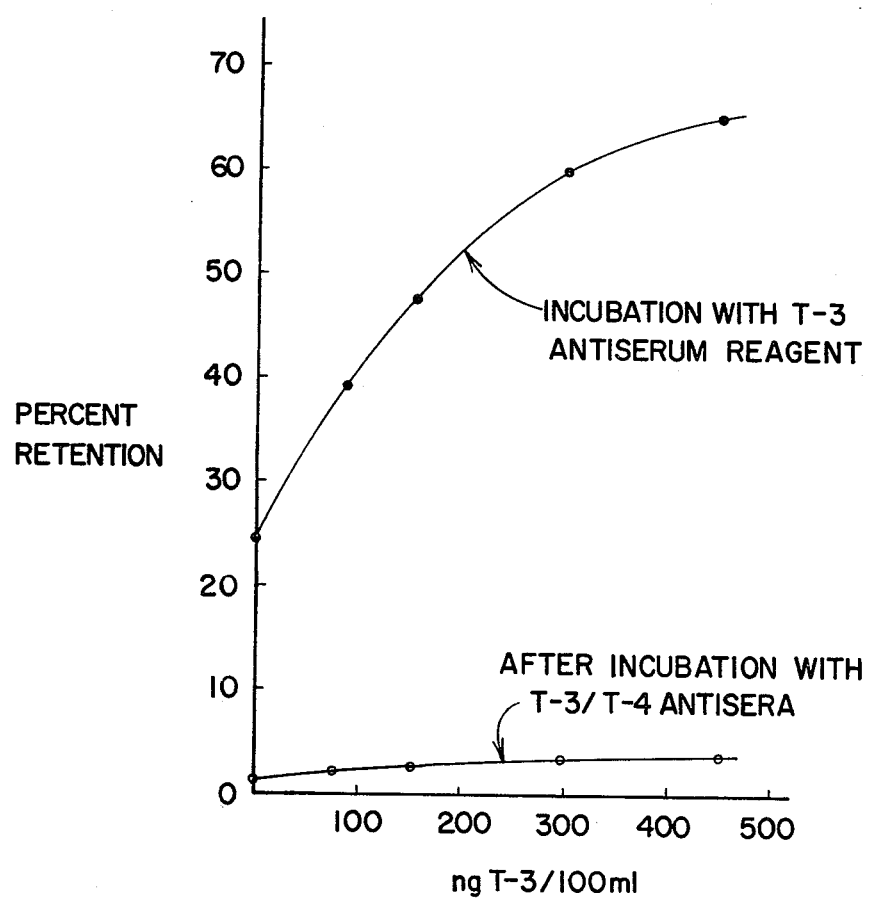
FIG. 2 is a graphical representation demonstrating the efficiency with which the excess T-3 antibody in the T-4 antibody incubation step removes potentially interfering radiolabeled T-3.

A significant amount of $^{125}$I T-3 retained on the column for the determination of T-3 interferes with the determination of $^{125}$I T-4 unless removed. This is accomplished by using a mixture of T-3 and T-4 antisera for the second antibody incubation following the T-3 determination. The T-3 antibody in the antisera mixture is present in excess and thereby elutes any residual $^{125}$I T-3 and T-3 from the column. Thus, any radioactivity remaining with the column after the final wash may be attributed to $^{125}$I T-4 alone. To demonstrate this, a series of columns were set up in which T-3 standards and $^{125}$I T-3 were removed by sequential incubations with T-3 antiserum (in the amount used in the actual assay procedure, i.e., containing a limiting amount of T-3 antiserum) and the T-3/T-4 antisera mixture (as used in the assay, i.e., containing an excess amount of T-3 antiserum) followed by buffer washes. Typical results are shown in FIG. 2 of the drawings illustrating that the T-3/T-4 antisera incubation effectively removed all radiolabeled T-3 from the column.

Accuracy

The accuracy of the combined T-3-T-4 radioimmunoassay method was examined through recovery studies and by comparison of assay results with values from reference methods. Table 3 below summarizes the results of experiments where the recovery of thyroid hormone added to serum specimens was determined.

The average overall recovery for T-3 and T-4 was 97.1 and 110.6%, respectively.

Serum T-3 values obtained from the combined T-3-T-4 RIA were compared with values obtained from two reference methods, SERALUTE Total T-3 RIA and Amersham/Searle T-3 RIA. With the SERALUTE method as the reference method, the least squares line was found to be described by the equation, $y = 0.84x - 36$. The correlation coefficient (r) and the standard error of estimate ($S_y$) were 0.98 and 23 ng/100 ml, respectively. With the Amersham/Searle method as the reference method, the least squares line was found to be described by the equation $y = 0.94x - 29$; r and $S_y$ were 0.85 and 28 ng/100 ml, respectively. When values from the SERALUTE method were compared with those from the Amersham method, the least squares line was described by the equation, $y = 1.19x + 3$, where r and $S_y$ were 0.93 and 22 ng/100 ml, respectively.

Serum T-4 values obtained from the combined T-3-T-4 RIA were compared with values obtained from Nuclear Medical Systems T-4 RIA and using the TETRA-LUTE Total T-4 test kit. The least squares line was described by the equation, $y = 0.96x + 0.06$. The correlation coefficient and standard error of estimate were 0.98 and 0.8 μg/100 ml, respectively,

TABLE 3

| Specimen No. | Recovery Of Triiodothyronine (T-3) and Thyroxine (T-4) | | | | | | | |
|---|---|---|---|---|---|---|---|---|
| | Endogenous | | Added | | Recovered | | % Recovered[a] | |
| | ng% T-3 | μg% T-4 | ng% T-3 | μg% T-4 | ng% T-3 | μg% T-4 | T-3 | T-4 |
| 1 | 28 | 3.1 | 343 | 11.4 | 327 | 13.3 | 95.3 | 116.7 |
| 1 | 28 | 3.1 | 171 | 5.7 | 169 | 6.7 | 98.8 | 117.5 |
| 1 | 28 | 3.1 | 86 | 2.9 | 78 | 3.8 | 90.7 | 131.0 |
| 2 | 117 | 6.9 | 171 | 5.7 | 156 | 5.8 | 91.2 | 101.8 |
| 3 | 70 | 6.0 | 171 | 5.7 | 175 | 4.9 | 102.3 | 86.0 |
| 4 | 6 | — | 343 | — | 337 | — | 98.3 | — |
| 5 | 54 | — | 171 | — | 176 | — | 102.9 | — |
| | | | | | | Overall Average | 97.1 | 110.6 |

[a] $\% \text{ Recovery} = \frac{\text{Total} - \text{Endogenous}}{\text{Added}} \times 100$

CONCLUSION

The results demonstrate that the present combined T-3-T-4 column RIA is capable of measuring the concentration of these hormones in serum specimens with acceptable sensitivity, precision and accuracy. In addition, the method is convenient since the same radioisotope is used as a tracer for both hormones and thus renders counting easier than a combined assay which relies on different radioisotopic tracers. Furthermore, the use of an excess amount of T-3 antibody with the limiting amount of T-4 antibody in the second incubation step is critical to the accuracy of the T-4 measurement.

What is claimed is:

1. A method for the combined radioimmunoassay for triiodothyronine (T-3) and thyroxine (T-4) in a serum or plasma sample comprising the steps of:
   (a) contacting a crosslinked dextran gel at a pH of at least 11 with said sample and with radiolabeled T-3 and T-4 labeled with the same radioisotope,
   (b) washing said gel with an alkaline aqueous solution having a pH less than 11,
   (c) incubating said gel with a predetermined first amount of an antibody to T-3 insufficient to bind all of the radiolabeled T-3 bound to said gel at the conclusion of step(b), (d) washing said gel with an alkaline solution having a pH less than 11, said gel retaining a portion of the radiolabeled T-3 bound thereto as a direct function of the amount of T-3 present in said sample, (e) incubating said gel with a predetermined second amount of an antibody to T-3 sufficient to bind all of the radiolabeled T-3 bound to said gel at the conclusion of step(d) and with a predetermined amount of an antibody to T-4 insufficient to bind all of the radiolabeled T-4 bound to said gel at the conclusion of step(d), (f) washing said gel with an alkaline aqueous solution having a pH less than 11, said gel retaining substantially no radiolabeled T-3 while retaining a portion of the radiolabeled T-4 bound thereto as a direct function of the amount of T-4 present in said sample, and (g) comparing (1) the relative amounts of radiolabeled T-3 and T-4 retained by said gel after washing steps(d) and (f), respectively, with respect to the amounts of radiolabeled T-3 and T-4 contacted with said gel in step(a), to (2) such relative amounts obtained by performing the same method on standard samples containing known amounts of T-3 and T-4.

2. The method of claim 1 wherein step(g) is accomplished by measuring the radioactivity of the incubating gel in step(c) ("first count"), of the incubating gel in step(e) ("second count"), and of the washed gel from step(f) ("third count"); by calculating T-3 and T-4 retention ratios as follows:

$$\text{T-3 retention} = \frac{\text{T-3 total count} - (\text{first count} - \text{second count})}{\text{T-3 total count}}$$

$$\text{T-4 retention} = \frac{\text{third count}}{\text{T-4 total count}}$$

wherein T-3 total count and T-4 total count are, respectively, the total radioactivity of the radiolabeled T-3 and T-4 contacted with the gel in step(a); and comparing such ratios to those obtained by performing the same method on standard samples containing known amounts of T-3 and T-4.

3. The method of claim 2 wherein T-3 total count is determined by separately performing the method of claim 1 through step(b), contacting the gel in step(a) with the radiolabeled T-3 but not the radiolabeled T-4 or the sample, and measuring the radioactivity of the washed gel after step(b), and wherein the T-4 total count is determined by separately performing the method of claim 1 through step(d), contacting the gel in step(a) with the radiolabeled T-4 but not the radiolabeled T-3 or the sample, and measuring the radioactivity of the washed gel after step(d).

4. The method of claim 1 wherein said dextran gel is crosslinked with an epihalohydrin and has a water regain of from about 1 to 5 grams per gram of dry gel.

5. The method of claim 1 wherein the wash solutions of steps(b), (d) and (f) are a buffer solution having a pH of between 7 and 10.

6. The method of claim 5 wherein said wash solutions are a barbital buffer solution having a pH of about 8.6.

7. The method of claim 1 wherein said radioisotope is radioactive iodine.

8. The method of claim 7 wherein said radioactive iodine is $^{125}I$.

9. The method of claim 1 wherein said gel is contained in a column and is washed in steps(b), (d), and (f) by passing said solutions through the column.

* * * * *